United States Patent
Goetz et al.

(10) Patent No.: US 7,623,919 B2
(45) Date of Patent: Nov. 24, 2009

(54) DISTRIBUTED LEAD FUNCTIONALITY TESTING

(75) Inventors: Steven M. Goetz, Brooklyn Center, MN (US); Nathan A. Torgerson, Andover, MN (US); Michael T. Lee, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 430 days.

(21) Appl. No.: 11/414,536

(22) Filed: Apr. 28, 2006

(65) Prior Publication Data

US 2006/0265024 A1  Nov. 23, 2006

Related U.S. Application Data

(60) Provisional application No. 60/676,187, filed on Apr. 29, 2005.

(51) Int. Cl.
*A61N 1/05* (2006.01)
(52) U.S. Cl. .............................. 607/27; 607/2
(58) Field of Classification Search ............ 607/27, 607/28, 2, 7, 8
See application file for complete search history.

(56) References Cited

U.S. PATENT DOCUMENTS

| | | | |
|---|---|---|---|
| 5,003,975 A | 4/1991 | Hafelfinger et al. | |
| 5,507,786 A | 4/1996 | Morgan et al. | |
| 5,534,018 A | 7/1996 | Wahlstrand et al. | |
| 5,593,431 A | 1/1997 | Sheldon | |
| 5,741,311 A | 4/1998 | Mc Venes et al. | |
| 5,755,742 A * | 5/1998 | Schuelke et al. | 607/27 |
| 5,891,179 A | 4/1999 | Er et al. | |
| 5,957,861 A | 9/1999 | Combs et al. | |
| 5,957,957 A | 9/1999 | Sheldon | |
| 6,188,927 B1 | 2/2001 | Lu et al. | |
| 6,317,633 B1 | 11/2001 | Jorgenson et al. | |
| 6,360,123 B1 | 3/2002 | Kimchi et al. | |

(Continued)

FOREIGN PATENT DOCUMENTS

EP  0 715 866 A2  6/1996

(Continued)

OTHER PUBLICATIONS

Notification of Transmittal of the International Search Report and the Written Opinion dated Oct. 11, 2006, for corresponding International Application No. PCT/US2006/016503, 11 pages.

(Continued)

*Primary Examiner*—Carl H Layno
*Assistant Examiner*—Brian T Gedeon
(74) *Attorney, Agent, or Firm*—Shumaker & Sieffert, PA

(57) ABSTRACT

Techniques for performing lead functionality tests, e.g., lead impedance tests, for implantable electrical leads are described. In some of the described embodiments, an implantable medical device determines whether a patient is in a target activity state, e.g., an activity state in which lead impedance testing will be unobtrusive, such as when a patient is asleep, or capture information of particular interest, such as when the patient is active, in a particular posture, or changing postures. The implantable medical device performs the lead functionality test based on this determination. Additionally, in some embodiments, the implantable medical device may group a plurality of measurements for a single lead functionality test into a plurality of sessions, and perform the measurement sessions interleaved with delivery of therapeutic stimulation.

26 Claims, 5 Drawing Sheets

U.S. PATENT DOCUMENTS

| | | |
|---|---|---|
| 6,490,486 B1 | 12/2002 | Bradley |
| 6,516,227 B1 | 2/2003 | Meadows et al. |
| 6,549,804 B1 | 4/2003 | Osorio et al. |
| 6,760,624 B2 | 7/2004 | Anderson et al. |
| 6,978,171 B2 | 12/2005 | Goetz et al. |
| 7,493,159 B2 * | 2/2009 | Hrdlicka et al. ............... 607/2 |
| 2002/0002389 A1 | 1/2002 | Bradley et al. |
| 2002/0120307 A1 | 8/2002 | Jorgenson et al. |
| 2002/0147473 A1 | 10/2002 | Seim et al. |
| 2002/0177881 A1 | 11/2002 | Conley et al. |
| 2003/0036772 A1 | 2/2003 | Saphon et al. |
| 2003/0125778 A1 | 7/2003 | Cho et al. |
| 2003/0176807 A1 | 9/2003 | Goetz et al. |
| 2004/0064161 A1 | 4/2004 | Gunderson et al. |
| 2004/0138711 A1 | 7/2004 | Osorio et al. |
| 2004/0162593 A1 | 8/2004 | Jorgenson et al. |
| 2005/0065554 A1 | 3/2005 | Kenknight et al. |
| 2005/0080460 A1 | 4/2005 | Wang et al. |
| 2005/0090870 A1 | 4/2005 | Hine et al. |
| 2005/0096704 A1 | 5/2005 | Freeberg |
| 2005/0222522 A1 | 10/2005 | Heruth et al. |
| 2006/0015148 A1 | 1/2006 | McCabe et al. |
| 2006/0264777 A1 | 11/2006 | Drew |
| 2006/0265025 A1 | 11/2006 | Goetz et al. |

FOREIGN PATENT DOCUMENTS

| | | |
|---|---|---|
| EP | 1 462 146 A1 | 9/2004 |
| WO | WO 03/077992 A1 | 9/2003 |
| WO | WO 2004/034883 A2 | 4/2004 |
| WO | WO 2006/041738 A2 | 4/2006 |

OTHER PUBLICATIONS

Reply to Written Opinion dated Feb. 28, 2007 for corresponding application PCT/2006/016503, (8 pgs.).

Notification of Transmittal of the International Preliminary Report on Patentability dated Jul. 5, 2007 for corresponding application PCT/2006/016503, filed Feb. 28, 2006 (9 pgs.).

Office Action dated Feb. 25, 2009 for U.S. Appl. No. 11/414,786 (7 pgs.).

Responsive Amendment dated Apr. 24, 2009 for U.S. Appl. No. 11/414,786 (11 pgs.).

Office Action dated Jun. 25, 2009 for U.S. Appl. No. 11/414,786 (7 pgs.).

Responsive Amendment dated Sep. 24, 2009 for U.S. Appl. No. 11/414,786 (12 pgs.).

* cited by examiner

DISTRIBUTED LEAD FUNCTIONALITY TESTING

This application claims the benefit of U.S. provisional application No. 60/676,187, filed Apr. 29, 2005, the entire content of which is incorporated herein by reference.

TECHNICAL FIELD

The invention relates to implantable medical devices and, more particularly, to testing of implantable electrical leads.

BACKGROUND

Implantable medical devices may be used to deliver therapeutic electrical stimulation to patients to treat a variety of symptoms or conditions, such as chronic pain, tremor, Parkinson's disease, epilepsy, incontinence, or gastroparesis. To treat such symptoms or conditions, an implantable medical device may deliver stimulation via electrical leads that include electrodes located proximate to the spinal cord, pelvic nerves, or stomach, or within the brain of a patient. In general, implantable medical devices deliver stimulation in the form of electrical pulses. Implantable medical devices coupled to electrode-carrying leads may additionally or alternatively be used to sense electrical activity within a patient.

An electrical lead may carry multiple electrodes, and each electrode may be coupled to a respective insulated conductor within the lead. An electrode, associated conductor, and tissue proximate to the electrode may form an "electrical path." The impedance of the various electrical paths provided by a lead may vary over the life of an implantable medical device due to, for example, material degradation or tissue growth proximate to the electrode. Further, a lead may develop a short between two or more conductors when insulation fails, or a conductor may fracture due to bending or other stresses placed on the lead by patient movement or manipulation.

Changes in lead impedance impair the ability of an implantable medical device to effectively sense electrical activity and/or deliver stimulation. Consequently, it may be desired to identify such changes in order to take corrective action, such as implantation of a new lead, or selection of different electrodes for sensing or delivery of stimulation. Traditionally, clinicians have used a programming device during an office visit to manually direct an implantable medical device to perform a lead integrity or functionality test. Manual lead functionality testing may include manually defining a plurality electrode combinations and, for each combination, directing the implantable medical device to measure the impedance presented by electrical paths the combination, or another electrical parameter for the combination, such as the current flowing through the electrical paths. The impedances, currents, or other electrical parameters of the various combinations may allow the clinician to identify changes in impedance or failures of the electrical path associated with a particular electrode.

Manual testing may be desired to confirm and maintain device efficacy, but is also very tedious. Because of the large number of possible electrode combinations that may be available on the one or more leads coupled to an implantable medical device, testing can take several minutes. During this time, therapeutic stimulation is generally not available, which can result in discomfort for or danger to the patient because symptoms are not suppressed.

Furthermore, significant changes in impedance, or other lead functionality issues, may occur between clinic visits, and may occur gradually over time. In some cases, such as where an implantable medical device is used for sensing, or to deliver deep brain stimulation, which are generally not perceivable by the patient, the patient may not detect a degradation of lead functionality. In such cases, the sensing or therapy may be inadequate for a significant period of time, e.g., until the next regularly-scheduled clinic visit, which may pose risks for the patient.

Also, a conductor short or fracture may be intermittent, and more likely to manifest during periods when the patient is changing posture, within a particular posture, or otherwise active. In such cases, a clinician may not be able to detect a conductor problem with a manual lead functionality test performed during an office visit. The existence of undiscovered conductor problems may limit the effectiveness of therapy and sensing, as discussed above.

SUMMARY

In general, the invention is directed to techniques for testing the functionality of implanted electrical leads. One or more implanted electrical leads may be coupled to a medical device that senses electrical activity or delivers electrical stimulation via electrodes carried by the leads. The medical device may automatically perform a lead functionality test, e.g., without receiving a command to perform the test from a user or programming device, outside of a clinic setting. In some embodiments, the medical device may advantageously perform such tests in a manner or at a time that may be less likely to disturb the patient in which the leads are implanted. Further, in some embodiments, the medical device may advantageously perform such tests in a manner or at a time such that the device is more likely to detect impairments of the functionality of leads, and particularly impairments that may be intermittent, such as an intermittent short or fracture of one or more of the conductors with the lead.

In some embodiments, the medical device determines whether a patient is in a target activity state based on a physiological sensor signal, e.g., one or more accelerometer signals. In such embodiments, the medical device performs a lead functionality test when the patient is in the target activity state. A target activity state may be one in which lead functionality testing will be unobtrusive because absent therapy will likely not be noticed, such as when a patient is asleep. Additionally or alternatively, a target activity state may be one during which a lead impedance test is more likely to capture information of particular interest. For example, the medical device may perform a lead functionality test when the patient is in a particular posture, or changing postures or otherwise active, which may allow the medical device to identify intermittent shorts and fractures. The medical device may perform the tests whenever it is determined that the patient is in the target activity state, or periodically based on a schedule that identifies how frequently lead functionality tests are to occur.

In some embodiments, the medical device may divide a plurality of measurements for a single lead functionality test into a plurality of sessions, which may be distributed over time. The medical device may interleave measurement sessions with delivery of therapeutic stimulation or sensing. By distributing the total time required for a lead functionality test over a plurality of distributed sessions, the consecutive length of time a patient is without stimulation or sensing may be reduced. For a patient with chronic pain, the shorter time periods without stimulation may be bearable, or even unnoticed.

For example, in some embodiments, a lead functionality test includes measuring one or more electrical parameters, such as impedance or current, for each of a plurality of combinations of electrodes. Over the course of a plurality of sessions, a medical device may make the measurements for all of the combinations. Each of the sessions includes measurements for one or more electrode combinations. The medical device may interleave such measurement sessions with, for example, therapeutic stimulation delivery such as individual electrical stimulation pulses or groups of stimulation pulses.

A lead functionality measurement test may include measurement of values for one or more electrical parameters, such as impedances or currents, associated with one or more of the electrodes carried by the leads. The medical device may store measured parameter values for later retrieval by a clinician, provide a message to a patient based on the measured parameter values, and/or modify a therapy based on the measured parameter values. The medical device may determine whether to perform any or all of these functions based on, for example, comparison of impedance magnitude or rate of change to a threshold.

The magnitude and rate of change values maintained by the medical device may be averages. In some embodiments, the medical device may maintain multiple average values calculated over longer and shorter periods of time for comparison to multiple thresholds. A shorter period average that exceeds a threshold, for example, may indicate a more severe problem that requires immediate attention, such as a lead fracture. In such case, the medical device may provide an alarm or message to the patient, e.g., via the implanted medical device or an external programmer, to cause the patient to visit a clinician.

In one embodiment, the disclosure provides a method comprising determining whether a patient is within a target activity state based on a physiological sensor signal, and automatically performing a lead functionality test for at least one electrical stimulation lead implanted within the patient when the patient is in the target activity state.

In another embodiment, the invention is directed to a system comprising at least one electrical stimulation lead implanted within a patient, a physiological sensor that generates a physiological sensor signal, and a processor that determines whether the patient is within a target activity state based on the physiological sensor signal, and initiates performance of a lead functionality test when the patient is within the target activity state.

In another embodiment, the disclosure provides a system comprising means for determining whether a patient is within a target activity state based on a physiological sensor signal, and means for performing a lead functionality test for at least one electrical stimulation lead implanted within the patient when the patient is within the target activity state.

In another embodiment, the disclosure provides a method for performing a lead functionality test for at least one electrical stimulation lead implanted within a patient comprising defining multiple combinations of electrodes, measuring an electrical parameter for each of the combinations over a series of measurement sessions, and delivering therapeutic stimulation to the patient via the electrical lead between consecutive measurements.

In another embodiment, the disclosure provides a system comprising at least one electrical stimulation lead implantable within a patient and a processor. The processor defines multiple combinations of electrodes that include electrodes carried by the electrical lead, controls measurement of an electrical parameter for each of the combinations over a series of measurement sessions, and directs delivery of therapeutic stimulation to the patient via the electrical lead between consecutive measurement sessions.

In another embodiment, the disclosure provides a system comprising means defining multiple combinations of electrodes that include electrodes carried by at least one implantable electrical lead, means for measuring an electrical parameter for each of the combinations of electrodes over a plurality of sessions, and means for delivering therapeutic stimulation to the patient via at least some of the electrodes between consecutive measurement sessions.

Embodiments of the invention may provide one or more advantages. For example, the invention may allow the duration of clinician office visits to be reduced because a clinician can receive results from lead functionality tests previously and automatically performed by an implantable medical device. In this manner, a clinician may evaluate lead functionality without needing to perform a test during the visit. The invention may also improve patient comfort by allowing testing to be scheduled over multiple short intervals and/or during a time a patient is likely to be sleeping.

Furthermore, the invention may allow for a more complete or detailed picture of the state of the lead system by providing long term averages and trends over time. For example, a gradual increase in measured impedance may indicate tissue build-up, while a sharp change could indicate a conductor short or fracture. The invention may also allow an intermittent lead failure to be detected. For example, lead impedance testing during the time that a patient is anticipated to be active, changing postures, or within a particular posture may detect intermittent failure that only occurs when patient is within such activity states. Additionally, the invention may allow for more rapid detection of lead problems. Once an implantable medical device detects a lead problem, it may proactively adjust delivered therapy and/or notify a patient to schedule a clinical visit, thereby minimizing the time the patient experiences sub-optimal therapy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
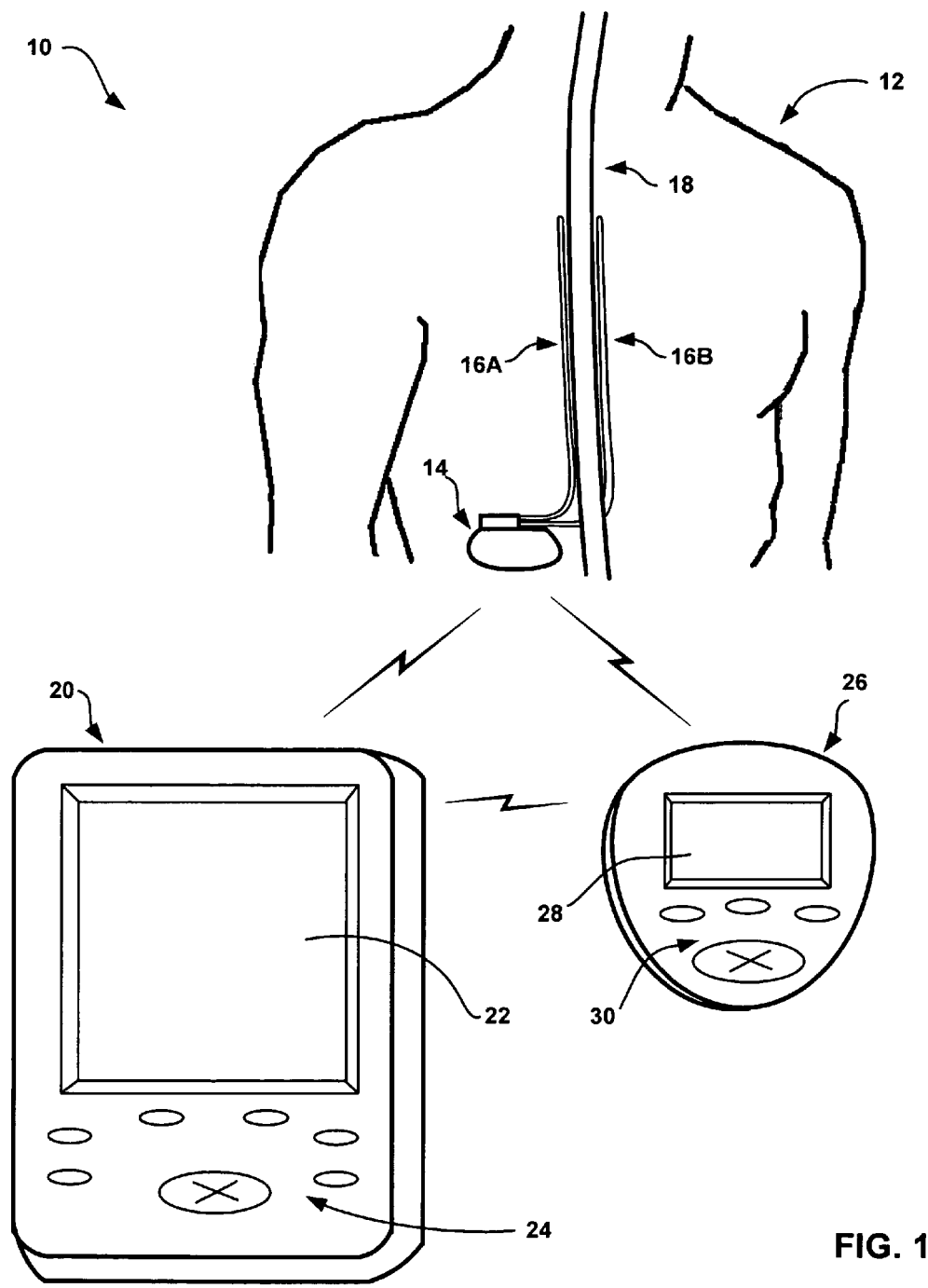
FIG. 1 is a conceptual diagram illustrating an example system that includes an implantable medical device that automatic performs lead functionality tests.

FIG. 1 is a conceptual diagram illustrating an example system 10 for automatically performing lead functionality testing for one or more electrical leads. System 10 includes an implantable medical device (IMD) 14 that delivers neurostimulation therapy to patient 12, a patient programmer 26, and a clinician programmer 20. As will be described in greater detail below, IMD 14 may perform lead functionality tests based on a determination that a patient is within a target activity state, and divide a lead functionality test into a plurality of temporally distributed sessions.

IMD 14 delivers neurostimulation therapy to patient 12 via electrical leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1, IMDs that deliver SCS therapy, or IMDs that deliver neurostimulation therapy. For example, one or more leads 16 may extend from IMD 14 to the brain (not shown) of patient 12, and IMD 14 may deliver deep brain stimulation (DBS) therapy to patient 12 to, for example, treat tremor, Parkinson's disease, epilepsy, or psychological disorders. As further examples, one or more leads 16 may be implanted proximate to the pelvic nerves (not shown) or stomach (not shown), and IMD 14 may deliver stimulation therapy to treat sexual dysfunction, urinary or fecal incontinence or gastroparesis. Leads 16 may include lead extensions, as needed.

Further, the invention is not limited to implementation via an implanted device, or a device that delivers stimulation. In some embodiments, an external medical device, such as an external trial stimulator, automatically performs lead functionality tests in accordance with the invention. In other embodiments, an implanted or external medical device may detect electrical activity within patient 12 via one or more leads, either as an alternative or in addition to delivering electrical stimulation via the leads.

System 10 also includes a clinician programmer 20. Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

A clinician (not shown) may use clinician programmer 20 to program neurostimulation therapy for patient 12. The clinician may also use clinician programmer 20 to program IMD 14 to later automatically perform lead functionality tests in accordance with the invention, e.g., outside of a clinic environment, as will be described in greater detail below.

System 10 also includes a patient programmer 26, which may, as shown in FIG. 1, be a handheld computing device. Patient programmer 26 may also include a display 28 and a keypad 30, to allow patient 12 to interact with patient programmer 26. In some embodiments, display 26 may be a touch screen display, and patient 12 may interact with patient programmer 26 via display 28. Patient 12 may also interact with patient programmer 26 using peripheral pointing devices, such as a stylus or mouse.

Patient 12 may use patient programmer 26 to control the delivery of neurostimulation therapy by IMD 14. For example, patient 12 may be able to select neurostimulation therapy programs, or modify program parameters such as pulse amplitude, width or rate, within limits set by a clinician. Patient programmer 26 may also provide patient 12 with information relating to the functional status of IMD 14. For example, patient programmer 26 may receive signals or information relating to the results of lead functionality testing from IMD 14, and inform patient 12 if leads 16 are functioning properly. In the event that leads 16 are not functioning properly, patient programmer 26 may automatically adjust the therapy delivered to patient 12, and/or indicate a problem and advise patient 12 to schedule a clinical visit. In some embodiments, IMD 14 may additionally or alternatively provide alerts to patient 12 or automatically adjust the therapy based on the results of lead functionality testing.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using RF telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

Figure 2:
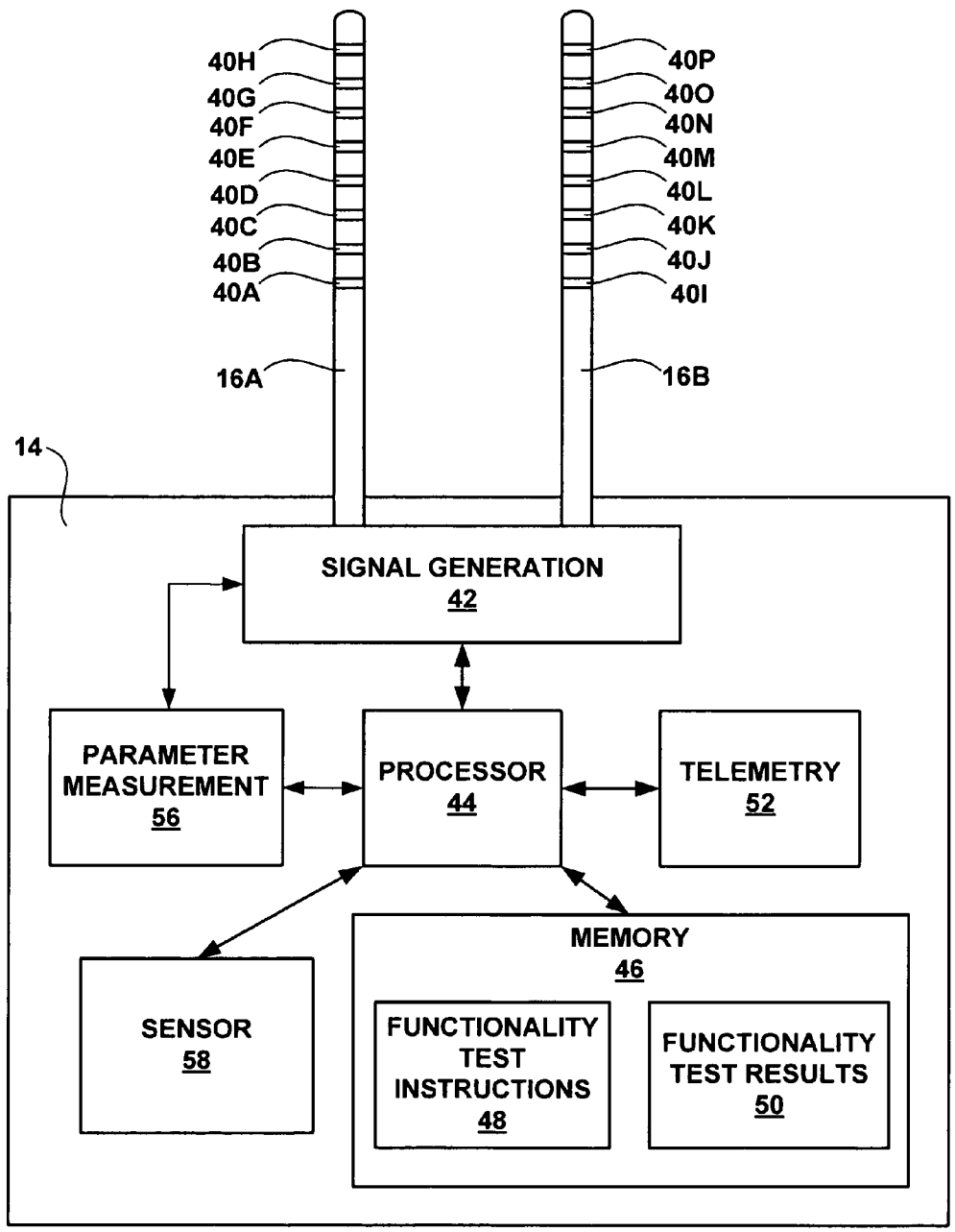
FIG. 2 is a block diagram further illustrating the implantable medical device of FIG. 1.

FIG. 2 is a block diagram illustrating an example configuration of IMD 14. IMD 14 may deliver neurostimulation therapy via electrodes 40A-H of lead 16A and electrodes 40I-P of lead 16B (collectively "electrodes 40"). Electrodes 40 may be ring electrodes. The configuration, type and number of electrodes 40 illustrated in FIG. 2 are exemplary, and other embodiments may comprise more or less leads, each lead having more or less electrodes than lead 16A and lead 16B (collectively "leads 16"). Further, in other embodiments, leads 16 may have other shapes, such as paddle-like shapes with electrodes located on one or more sides of the paddle, or may include complex, multi-dimensional electrode array geometries.

IMD 14 includes a signal generation circuitry 42, a processor 44, a memory 46, telemetry circuitry 52, electrical parameter measurement circuitry 56 and a physiological sensor 58. Electrodes 40 are electrically coupled to signal generation circuitry 42 via conductors within leads 16. Each of electrodes 40 may be coupled to signal generation circuitry 42 via a separate insulated conductor (not shown). Each of electrodes 40, its associated conductor, and proximate tissue form an electrical path.

Signal generation circuitry 42 may deliver electrical signals, e.g., electrical pulses, via two or more of electrodes 40, e.g., two or more electrical paths, one or more of which are return paths. Signal generation circuitry 42 may include, for example, one or more output pulse generators, and switches or the like to couple the pulse generators to selected electrodes. Signal generation circuitry 42 may deliver the signal to patient 12 via selected combinations of electrodes 40 under the control of processor 44.

Processor 44 controls signal generation circuitry 42 to deliver therapeutic stimulation to patient 12, e.g., neurostimulation therapy in the form of electrical pulses. Processor 44 may also control signal generation circuitry 42 to deliver non-therapeutic signals for lead functionality testing, which may also be in the form of electrical pulses, as will be described in greater detail below. In some embodiments, IMD 14 may additionally include signal detection circuitry (not shown) that detects electrical signals within patient 12 via electrodes 40. Electrodes 40 may be electrically coupled to such signal detection circuitry via conductors within leads 16. As discussed above, the invention is not limited to embodiments in which IMD 14 delivers therapeutic stimulation to patients, and includes embodiments in which IMD 14 monitors electrical signals within patient 12 instead of or in addition to delivery of therapeutic stimulation. However, even in embodiments in which IMD 14 does not deliver therapeutic stimulation, IMD 14 may nonetheless include signal generation circuitry 42 to deliver non-therapeutic signals for lead functionality testing.

Processor 44 may control the delivery of therapeutic stimulation according to programs or program parameters selected by a clinician and/or patient using one of programmers 20, 26. For example, stimulation therapy programs comprising parameters, such as pulse amplitude, pulse width, pulse rate and electrode polarity, may be received from one or both of the programmers and stored in memory 46. Further, adjustments to parameters or selection of programs may be received from the programmers, and the programs stored in memory 46 may be modified accordingly. As illustrated in FIG. 2, IMD 14 may include telemetry circuitry 52 that facilitates communication, e.g., radio-frequency or inductive communication, between processor 44 and programmers 20, 26.

Processor 44 also automatically initiates lead functionality testing according to lead functionality test instructions 48, which are stored in memory 46. Processor 44 also stores lead functionality test results 50 in memory 46. Processor 44 may receive lead functionality test instructions 48 from clinician programmer 20 via telemetry circuit 52 during programming by a clinician. Lead functionality test instructions 48 may include information identifying combinations of electrodes 40 for lead functionality testing, and instructions that indicate when to perform a lead functionality test.

Processor 44 may include any one or more of a microprocessor, digital signal processor (DSP), application specific integrated circuit (ASIC), a field-programmable gate array (FPGA), or equivalent discrete or integrated logic circuitry. Memory 46 may store program instructions that, when executed by processor 44, cause processor 44 and IMD 14 to provide the functionality attributed to them herein. Memory 46 may include any volatile, non-volatile, magnetic, optical, or electrical media, such as any one or more of a random access memory (RAM), read-only memory (ROM), non-volatile RAM (NVRAM), electronically-erasable programmable ROM (EEPROM), flash memory, or the like.

A lead functionality test may include testing a plurality of combinations of electrodes 40. In general, it is desirable to test each possible combination of two of electrodes 40 during a lead functionality test. However, combinations of more than two of electrodes 40 are possible. A combination may also include only one of electrodes 40 and an electrode integrated with the outside shell, housing, or "can," of IMD 14, but such monopolar testing may not provide evidence of a short between two conductors in leads 16.

For each combination, processor 44 may control signal generation circuitry 42 to deliver a non-therapeutic, e.g., sub-threshold, pulse via the electrodes 40 of the combination, and control parameter measurement circuitry 56 to measure a value of an electrical parameter during the pulse. A sub-threshold pulse may be, for example, a pulse having an amplitude or pulse width significantly lower than that of therapeutic stimulation pulses. Because of their low amplitude and/or pulse width, such dedicated pulses may not result in any therapeutic or adverse effects, e.g., may not be above a threshold sufficient to activate any nerves or other tissues, and therefore may be referred to as "sub-threshold" pulses. The measured electrical parameter may be, for example, the impedance presented by the combination of electrodes or the current through the combination of electrodes during delivery of the pulse. Parameter measurement circuitry 56 may include resistors, capacitors, or other known circuitry for sampling and/or holding a value of an electrical parameter, which may be coupled in series or parallel with signal generation circuitry 42 for measurement of one or both of voltage or current when the pulse is delivered by the circuitry.

Processor 44 may determine the impedance or current based on the measured voltage and/or current using any of a variety of know techniques. For example, in some embodiments, signal generation circuitry 42 delivers a voltage pulse with a decay, and measurement circuitry 56 samples and holds the final voltage value of the pulse at the end of the pulse. Based on the initial, e.g., programmed, voltage for the pulse, and the sampled final voltage, processor 44 may determine the impedance presented by the combination of electrodes using known techniques, such as those described in commonly-assigned U.S. Pat. No. 6,978,171, which issued to Goetz et al. on Dec. 20, 2005, which is incorporated by reference herein in its entirety. Equations or the like used by processor 44 to determine the impedance or current may be stored in memory 46.

Alternatively, lead functionality test instructions 48 may instruct processor 44 to perform a lead functionality test, e.g., impedance test, specifically with the one or more combinations (two or more) of electrodes 40 currently being used to deliver therapy to patient 12. For such testing, processor 44 may control measurement circuitry 56 to be coupled to signal generation circuitry 42 and measure the impedance of the combination during a therapeutic pulse.

Lead functionality test instructions 48 contain instructions for processor 44 to perform lead testing when patient 12 is within a target activity state. Target activity states may include, as examples, asleep or active, e.g., the patient is exercising. Target activity states may also include a target posture, or when the patient is changing postures. It may be desirable to perform lead functionality testing during a time when a patient is sleeping in order to reduce patient discomfort due to the absence of neurostimulation therapy during testing. It may also be desirable to perform lead functionality testing during a time when a patient is active, changing postures, or within a particular posture, because intermittent lead failures might only be detectable during such activity states. In some embodiments, lead functionality test instructions 48 may contain instructions for lead functionality testing during two or more target activity states.

Physiological sensor 58 generates a signal as a function of patient physiological parameter, such as activity and/or posture. Processor 44 may determine whether patient 12 is within the target activity state based on the signal generated by sensor 58. As examples, sensor 58 may comprise electrodes or other known sensors for detecting heart rate or respiration rate, a motion sensor, e.g., piezoelectric motion sensor, or other known sensor that may provide evidence of a patient's activity level. In some embodiments, sensor 58 may be a multi-axis accelerometer capable of detecting patient posture and posture changes, as well as gross body movement and footfalls. Further information regarding use of multi-axis accelerometers to determine patient posture may be found in a commonly-assigned U.S. Pat. No. 5,593,431, which issued to Todd Sheldon on Jan. 14, 1997, and is incorporated herein by reference in its entirety.

Although illustrated as including a single sensor 58, IMD 14 may include a plurality of physiological sensors 58, and processor 44 may determine whether patient 12 is within a target activity state based on the signals from the plurality of sensors 58. The one or more sensors 58 may be located within a housing of IMD 14, as suggested by FIG. 2, or coupled to IMD 14 via leads or wireless communication.

As examples, processor 44 may determine that patient 12 is changing postures based on changes in signals output by a multi-axis accelerometer, or within a target posture based on a comparison of signals output by the multi-axis accelerometer to templates or thresholds stored in memory 46. Processor 44 may determine whether patient 12 is within a target high activity state or sleeping by comparing, as examples, one or more of activity counts derived from an accelerometer or piezoelectric crystal signal, a heart rate, a heart rate variability, a respiration rate, or a respiration rate variability to threshold values stored in memory 46. Furthermore, IMD 14 may include any of the sensors, and processor 44 may determine whether patient is asleep, using any of the techniques described in commonly-assigned U.S. patent application Ser. No. 11/081,786 by Heruth et al., filed Mar. 16, 2005, the entire content of which is incorporated herein by reference.

During delivery of a non-therapeutic pulse to an electrode combination for lead functionality testing, signal generation circuitry 42 may be unable to deliver therapeutic stimulation. In some embodiments, lead functionality test instructions 48 instruct processor 44 to divide a lead functionality test that includes a plurality of electrode combinations into multiple sessions. In this manner, IMD 14 may limit the length of each testing session, such that patient 12 would not notice the absence of therapy delivered by the IMD. For example, a testing session may be limited to one second or less.

Figure 5:
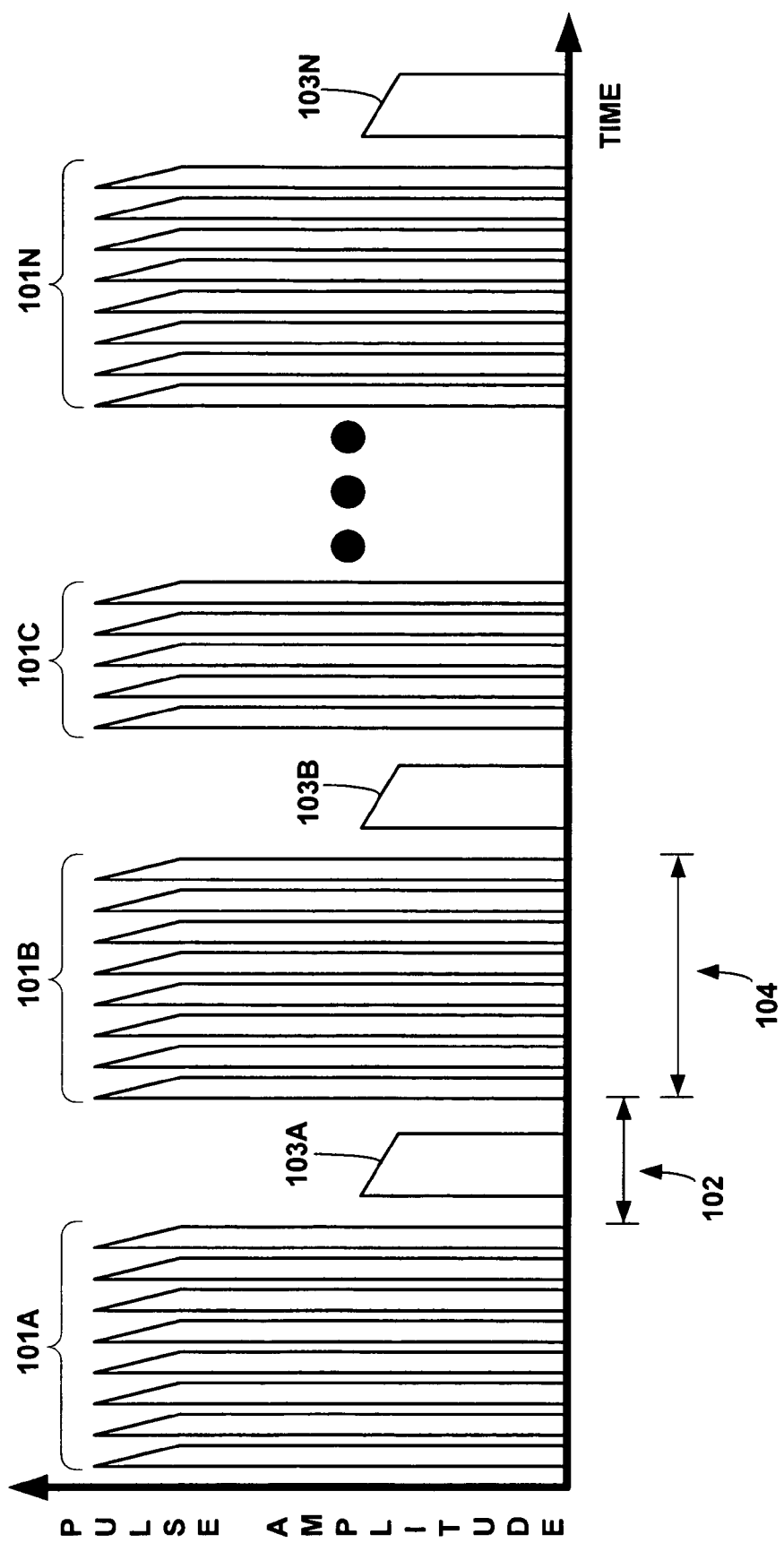
FIG. 5 is a timing diagram illustrating therapeutic stimulation delivered to a patient by an implantable medical device between sessions of a lead functionality test according to an example embodiment of the invention.

A non-therapeutic pulse for lead functionality testing, e.g., to measure impedance for a combination of electrodes, can occur in less than one-tenth of a second. Therefore, multiple sets of electrodes can be tested in a testing session even if the testing session is no more than one second. However, in some embodiments, as shown in FIG. 5, testing sessions may be limited to only a single combination of electrodes and single pulse. Dividing a plurality of electrode combinations for lead impedance testing into multiple sessions may be especially useful when a patient is in a high activity state, because a patient may experience the most discomfort with an absence of neurostimulation therapy when the patient is at a hightly active level.

Lead functionality test instructions 48 may also include a schedule that instructs processor 44 to repeat testing at regular intervals. For example, lead functionality test instructions 48 may require that a lead functionality test on each possible combination of electrodes occur at least once a day. In embodiments where lead functionality tests are divided into multiple sessions, IMD 14 may repeat each session at least once a day.

The results of lead functionality testing are stored in memory 46 as lead functionality test results 50. In this manner, lead functionality test results 50 may contain a history of lead functionality testing, e.g., measured impedance, current or other values, or averages of such values. Lead functionality test results 50 may also include information identifying the time and date the results were obtained, as well as other information relating to the conditions under which the lead functionality test was performed. For example, the activity levels or postures assumed patient 12 during a lead functionality test may be stored in memory in association with the results. A history of lead functionality testing may allow IMD 14, or a clinician or patient using clinician programmer 20 and/or patient programmer 26 to detect an intermittent lead failure or tissue formed around one of electrodes 40.

IMD 14 can transmit the results of lead impedance tests to patient programmer 26 and/or clinician programmer 20. In some embodiments, a programmer, e.g., patient programmer 26, may interpret the results of the tests to determine if the impedances are within acceptable values. In other embodiments, IMD 14 may determine if impedances are within acceptable values, e.g., stored in memory 46, and communicate this determination to patient programmer 26 and/or clinician programmer 20. For example, high impedance may indicate a conductor fracture or tissue growth around an electrode, while relatively low impedance can indicate a short between conductors in a lead. In either case, if the result of a lead impedance test indicates degraded lead functionality, the programmer may provide an indication of degraded lead functionality.

If test results 50 or other signals received from IMD 14 indicate a significant change in lead functionality, patient programmer 26 may provide a message instructing the patient to schedule a clinical visit. Additionally or alternatively, IMD 14 may include circuitry for communication with patient 12, e.g., by emitting an audible, vibratory, or perceivable electrical stimulation signal, and processor 44 may alert patient 12 of a detected lead fault via such a signal when the results indicate a significant change in lead functionality. In either case, system 10 may provide patient 12 with a message indicating that a clinical visit is needed to address a significant lead fault, rather than waiting for the lead fault to be discovered when IMD 14 is interrogated by clinician programmer 20 for lead functionality test results 50 at the next scheduled clinic visit.

Additionally or alternatively, in some embodiments, system 10 may include devices for networked communcation between IMD 14 and/or programmer 26 on one hand, and a remote clinic or other monitoring service on the other. In this manner, test results, lead fault indications, or other lead functionality information may be more quickly provided from an IMD to a clinician or the like, who may determine what course of action to follow to address any changes in lead functionality. In some cases, such a networked system may be used by a clinician to reprogram an IMD remotely, in order to address a change in lead functionality without requiring the patient to visit a clinic.

Furthermore, IMD 14, patient programmer 26 and/or clinician programmer 20 may modify patient therapy to compensate for degraded lead functionality. For example, if an electrode conductor within one of leads 16 has a fracture, electrodes coupled to conductor may be "locked-out," such that IMD 14 does not deliver stimulation via the electrodes, and user cannot direct the IMD to deliver stimulation via the electrodes. Stimulation therapies provided by IMD 14 can be adjusted to utilize combinations of electrodes that do not include electrodes having faulty conductors. If an electrode is surrounded by tissue growth, stimulation therapy can be adjusted to increase the amplitude for stimulation programs that use that electrode. In some embodiments, adjustment to patient therapy may be performed automatically by IMD 14, patient programmer 26 and/or clinician programmer 20. In other embodiments a clinician or patient may manually adjust patient therapy using one of the programmers.

If test results 50 or other signals received from IMD 14 indicate a significant change in lead functionality, processor 44 may automatically control performance of one or more follow-up measurements, either on the specific electrodes identified as experiencing a functionality change by the original test, or all electrodes. The follow-up measurement may occur at a scheduled time, or when patient 12 is again within the target activity state, e.g, within same posture as the original test. Processor 44 may use such follow-up measurements to confirm a lead functionality problem prior to taking actions such as, for example, notifying a user or modifying therapy. Processor 44 may require three or more consistent tests before taking such actions.

Lead functionality test results 50 may include a large amount of data. In some embodiments, IMD 14 may keep the results of all lead functionality tests in memory 46 for an indefinite period. In other embodiments, test results 50 may be stored in a compressed format within memory 46. For example, IMD 14 may clear memory 46 of lead functionality test results 50 once IMD 14 has transmitted the content of lead impedance test results 50 to patient programmer 26 or clinician programmer 20 in order to minimize the amount of memory 46 required by IMD 14 to store lead functionality test results 50. Other memory management techniques are also possible. For example, in some embodiments, IMD 14 may delete lead functionality test results 50 only if instructed by a clinician or after transmitting lead impedance test results 50 to clinician programmer 20.

Some embodiments provide patient 12 and/or a clinician an additional option to manage memory 46, including memory used to store lead functionality test results 50. For example a clinician may instruct IMD 14 to keep lead functionality test results 50 in memory 46 until transmitted to clinician programmer 20, or to keep only the most recent or significant results in the event that memory 46 becomes full. For example, significant results could include those that show changes in measured impedance for a particular set of electrodes. Further, processor 44 may reduce the size of lead functionality test results 50 within memory by maintaining one or more averages for measured electrical parameters, such as impedances or currents, rather than each measured value.

Figure 3:
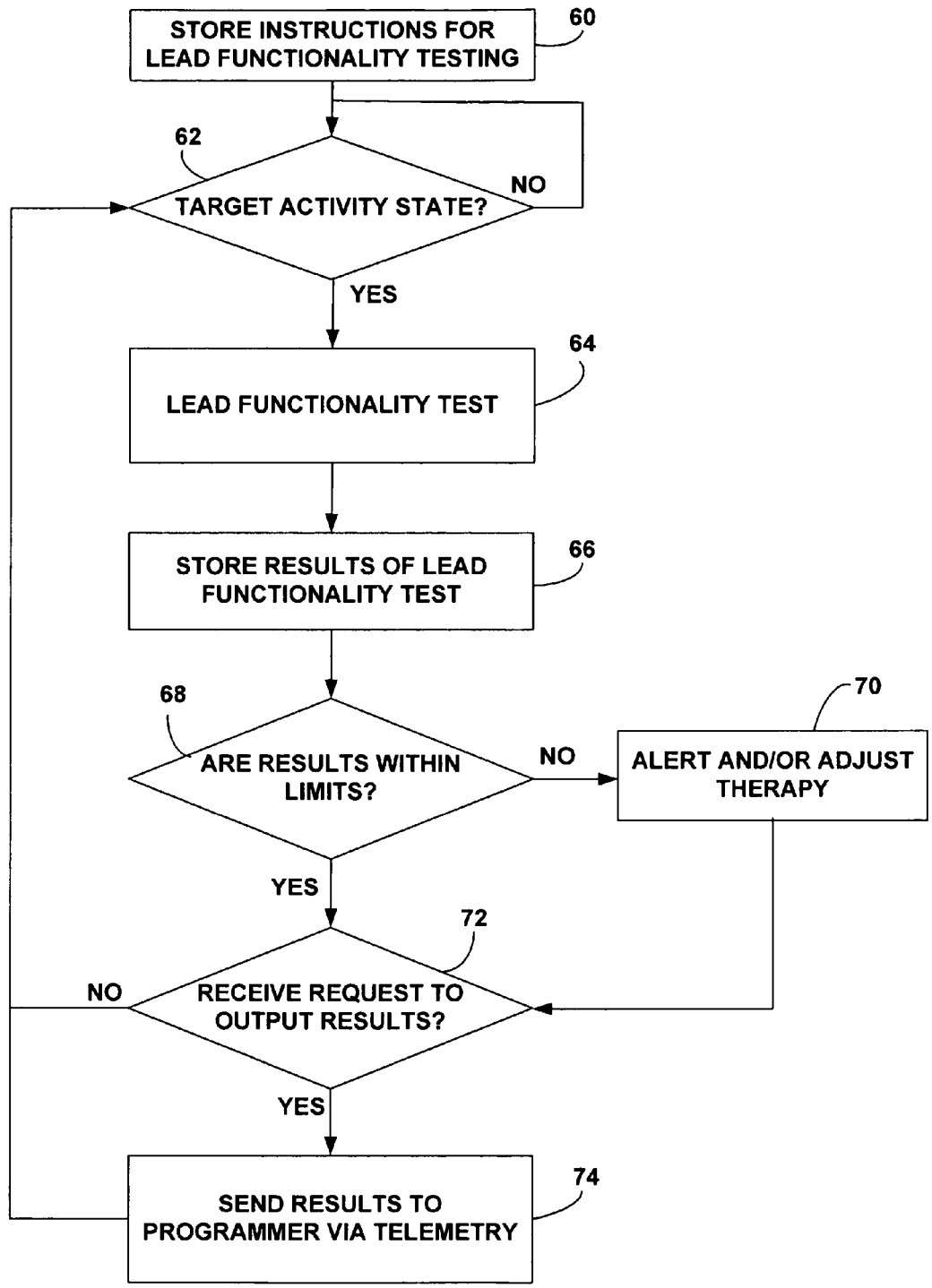
FIG. 3 is a flow diagram illustrating an example method for automatically performing lead functionality tests when a patient is within a target activity state.

FIG. 3 is a flow diagram illustrating an example method for automatically performing lead functionality testing according to the invention. For example, the described method may be used by IMD 14 in FIGS. 1 and 2 to automatically perform lead functionality testing. First, an IMD stores instructions for lead functionality testing (60). For example, a clinician may use clinician programmer 20 (FIG. 1) to send lead functionality testing instructions to the IMD. As described with respect to IMD 14 in the description of FIG. 2, such instructions can contain a variety of commands. For example, the stored instructions may instruct IMD 14 to perform lead functionality testing when a patient is within a target activity state. In some embodiments, the stored instructions may require lead functionality testing for two or more target activity states. Additionally, the stored instructions may divide a lead functionality test for a plurality of electrode combinations into multiple sessions. For example, each testing session may be limited to one second or less, which may reduce patient discomfort caused by an absence of therapy during the lead functionality testing.

IMD 14 monitors for a target activity state (62). The target activity state may be defined by the instructions stored by the IMD. Different embodiments of the invention may provide different techniques for determining whether the patient is in a target activity state. For example, the activity state of a patient may be determined using a heart rate sensor, respiration sensor, motion sensor, or other physiological sensor, as discussed above. In some embodiments, a plurality of physiological parameters, and associated sensors and techniques, may be used in combination to improve accuracy in determining the activity state of the patient. As discussed above, examples of target activity states are sleeping, active, changing postures, or a particular posture.

When IMD 14 determines that the patient is in a target activity state, the IMD performs lead functionality testing according to the instructions (64). Lead functionality testing, e.g., lead impedance or current testing, may be performed using any known techniques, such as those described above with reference to FIG. 2. For example, to perform lead impedance testing, the IMD may deliver a non-therapeutic pulse via a combination of two electrodes, measure final voltage or current amplitude for the pulse, and determine an impedance for the combination based on the measured final amplitude. Testing may be repeated for a plurality of electrode combinations and/or for the same combinations of electrodes on multiple occasions according to the instructions stored by the IMD.

After performing the lead functionality test, the IMD stores the results of the test in memory (66). The IMD may also determine if the lead functionality test results are within limits defined by the stored instructions (68). The IMD may compare measured impedance or current values for one or more combinations, or one or more averages determined based on such values, to one or more threshold values stored in a memory of the IMD. Further, the IMD may compare a rate of change for an average impedance or current value to one or more threshold values stored in a memory of the IMD. In some embodiments, the IMD may maintain multiple average values calculated over longer and shorter periods of time in a memory for comparison to multiple thresholds. A shorter period average that exceeds a threshold, for example, may indicate a more severe problem that requires immediate attention, such as a lead fracture.

If one or more of the test results are outside limits defined by the instructions, thresholds or other information stored in the IMD memory, the IMD may adjust patient therapy, store an alert that the patient or a clinician will receive the next time a programmer communicates with the IMD, cause a patient programmer to immediately alert the patient, or directly provide some other audible, vibratory, or stimulation alert to the patient, e.g., via the IMD (70). For example, if an electrode conductor has a fracture, the IMD may stop delivering therapies that use that electrode. If an electrode has been surrounded by fibrous or other tissue growth, which may cause an increase in the measured or average impedances associated with that electrode, the IMD may increase the voltage or current amplitude for therapies that use that electrode.

The IMD may also determine whether a user has requested the stored lead functionality test results, e.g., whether a clinician or patient has requested the results using a clinician or patient programmer (72). In response to such a request, the IMD will send the results to the programmer 20, 26 or another external device (74), where they may be presented as a trend diagram, histogram, or any other graph. In some embodiments, the IMD will send lead functionality test results to programmer or other a device whenever communicating with such a device, e.g., without receiving a specific request for the results. Further, while the method shown in FIG. 3 illustrates the IMD monitoring for a request to send stored results after storing a result (66), IMD may receive requests to export results stored in a memory at any time.

Figure 4:
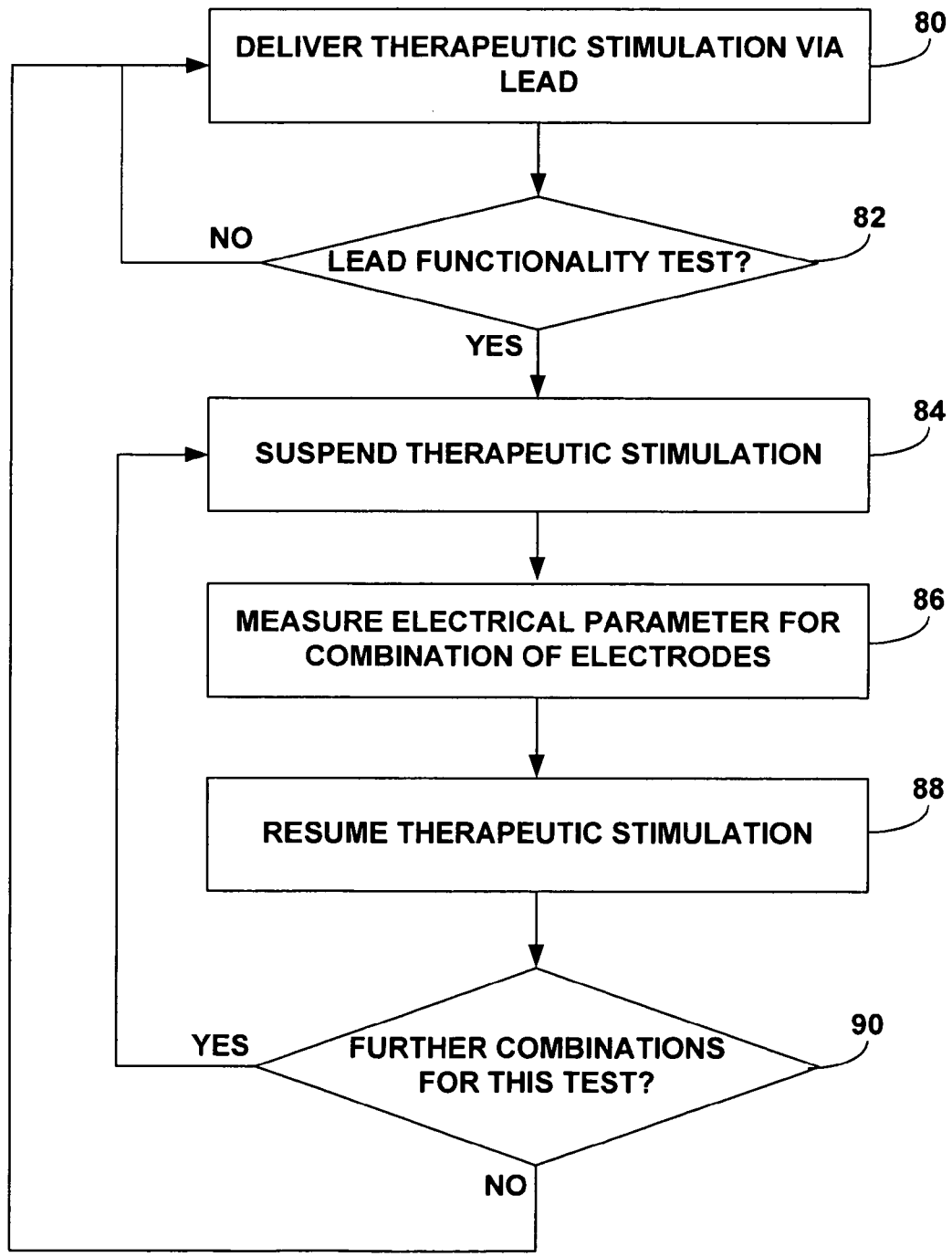
FIG. 4 is a flow diagram illustrating an example method for performing a lead functionality test.

FIG. 4 is a flow diagram illustrating an example method for performing a lead functionality test. More particularly, FIG. 4 illustrates an example method that may be employed by an IMD or other medical device to divide a plurality of measurements for a single lead functionality test into a plurality of sessions, which may be distributed over time, and interleaved with delivery of therapeutic stimulation or sensing.

A lead functionality test may include iteratively combining electrodes from one or more leads, and testing each combination. A complete lead functionality test may include testing all or a substantial majority of the possible combinations, e.g., pairs, of electrodes from one or more leads. According to the example method, the total number of tests for a single, complete lead functionality test, e.g., the total number of combinations, may be distributed over time in a plurality of discrete sessions that are interleaved with electrophysiological sensing or therapeutic stimulation delivery.

In the illustrated example, the IMD delivers therapeutic stimulation to a patient through electrodes carried by at least one lead (80). In response to determining that a lead functionality test is to be performed (82), e.g., detecting that the patient is within a target activity state, the IMD suspends the delivery of therapeutic stimulation (84). The IMD may then measure one of more electrical parameters for a first combination of the electrodes (86). For example, the a processor of the IMD 14 may control signal generation circuitry 42 to deliver a sub-threshold pulse via the first combination of electrodes, and use measurement circuitry 56 measure an impedance for the first combination, as described above. The IMD may then resume delivery of therapeutic stimulation (88). If the IMD determines that further combinations of electrodes need to be tested for the present lead functionality test (90), the IMD may again suspend therapy (84), and measure an electrical parameter for a next combination of electrodes (86). The IMD may continue suspending, measuring and resuming (84-88) so long as further combinations of electrodes need to be tested for the present lead functionality test. When the present lead functionality test is complete (90), the IMD may continue to deliver therapeutic stimulation (80) until it is time to automatically perform another lead functionality test (82).

FIG. 5 is a timing diagram showing amplitude of pulses delivered to a patient by an IMD delivering therapy and performing a lead impedance test according to an embodiment of the invention. More particularly, FIG. 5 illustrates therapeutic stimulation periods 101A-101N (collectively "stimulation periods 101") in which stimulation is delivered in the form of electrical pulses, and lead functionality testing pulses 103A-103N (collectively "testing pulses 103"). In other words, FIG. 5 illustrates a plurality of measurements for a lead functionality test divided into a plurality of sessions over time, which are interleaved with delivery of therapeutic stimulation. The delivery of pulses illustrated in FIG. 5 may be a result of an IMD performing the example method of FIG. 4.

The pulses delivered by an IMD during therapeutic stimulation periods 101 may be neurostimulation therapy pulses. In general, the IMD continuously delivers therapeutic stimulation, except for short interruptions required to perform lead functionality testing with the temporally-distributed testing pulses 203. Lead functionality testing pulses 203 may be non-therapeutic, e.g., may occur at sub-threshold voltage or current amplitudes such that the patient can not feel the pulses. The IMD may deliver each of testing pulses 203 via a different one of a plurality of electrode combinations that are to be tested during a lead functionality test. For example, the IMD may deliver one of pulses 203 for every unique pairing of the electrodes coupled to the IMD.

In the illustrated example, each session includes only a single testing pulse 203, i.e., tests only a single combination of electrodes. In other embodiments, more than one combination of electrodes may be tested by delivering more than one pulse 203 during each session. In any case, dividing the testing of a plurality of electrode combinations into multiple sessions may increase patient comfort by preventing noticeable disruptions to patient therapy during lead functionality testing.

A duration 102 of each testing session may within a range from approximately 200 microseconds to approximately five minutes. For example, duration 102 may be less than approximately one second. Duration 102 may be approximately equivalent to a single electrical pulse. A time period 104 between adjacent sessions may be within a range from approximately ten seconds to approximately thirty minutes. For example, time period 104 may be greater than approximately thirty seconds, or greater than approximately one minute.

Various embodiments of the invention have been described. These and other embodiments are within the scope of the following claims.

The invention claimed is:

1. A method for performing a lead functionality test for at least one electrical lead implanted within in a patient comprising:

defining multiple combinations of electrodes to test during a lead functionality test, each of the combinations of electrodes including at least one electrode carried by the at least one electrical lead; and measuring an electrical parameter for each of the combinations over a series of measurement sessions, wherein measuring the electrical parameter for each of the combinations over a series of measurement sessions comprises:

suspending delivery of therapeutic stimulation during each of the measurement sessions;

controlling measurement of the electrical parameter for a different one or more of the combinations during each of the measurement sessions; and resuming the delivery of the therapeutic stimulation to the patient via the electrical lead between consecutive measurement sessions.

2. The method of claim 1, wherein measuring an electrical parameter comprises measuring an impedance.

3. The method of claim 1, wherein a duration of each of the sessions is within a range from approximately 200 microseconds to approximately five minutes.

4. The method of claim 1, wherein a duration of each of the sessions is less than approximately one second.

5. The method of claim 1, wherein each of the sessions includes a single electrical pulse.

6. The method of claim 1, wherein a time period between adjacent ones of the plurality of sessions is within a range from approximately ten seconds to approximately thirty minutes.

7. The method of claim 1, wherein a time period between adjacent ones of the plurality of sessions is greater than approximately thirty seconds.

8. The method of claim 1, wherein a time period between adjacent ones of the plurality of sessions is greater than approximately one minute.

9. The method of claim 1, wherein delivering therapeutic stimulation comprises delivering neurostimulation pulses.

10. The method of claim 1, further comprising providing lead functionality information to a user based on the lead functionality test.

11. A system comprising:

at least one electrical lead implantable within a patient; and a processor that:

defines multiple combinations of electrodes to test during a lead functionality test, each of the combinations of electrodes including at least one electrode carried by the at least one electrical lead; and controls measurement of an electrical parameter for each of the combinations over a series of measurement sessions, wherein, in controlling of the measurement of an electrical parameter for each of the combinations over a series of measurement sessions, the processor:

suspends delivery of therapeutic stimulation during each of the measurement sessions, controls measurement of the electrical parameter for a different one or more of the combinations during each of the measurement sessions, and directs delivery of the therapeutic stimulation to the patient via the electrical lead between consecutive measurement sessions.

12. The system of claim 11, wherein the electrical parameter comprises an impedance.

13. The system of claim 11, wherein a duration of each of the sessions is within a range from approximately 200 microseconds to approximately five minutes.

14. The system of claim 11, wherein a duration of each of the sessions is less than approximately one second.

15. The system of claim 11, wherein each of the sessions includes a single electrical pulse.

16. The system of claim 11, wherein a time period between adjacent ones of the plurality of sessions is within a range from approximately ten seconds to approximately thirty minutes.

17. The system of claim 11, wherein a time period between adjacent ones of the plurality of sessions is greater than approximately thirty seconds.

18. The system of claim 11, wherein a time period between adjacent ones of the plurality of sessions is greater than approximately one minute.

19. The system of claim 11, further comprising an implantable medical device coupled to the lead that includes the processor.

20. The system of claim 11, wherein the processor controls delivery of neurostimulation pulses by the implantable medical device between each of the sessions.

21. The system of claim 11, wherein the processor provides lead functionality information to a user based on the lead functionality test.

22. The system of claim 11, wherein the processor directs delivery of a plurality of therapeutic stimulation pulses to the patient via the electrical lead between consecutive measurement sessions.

23. A system comprising:

means defining multiple combinations of electrodes to test during a lead functionality test, each of the combinations of electrodes including at least one electrode carried by at least one implantable electrical lead; and means for measuring an electrical parameter for each of the combinations of electrodes over a series of measurement sessions, wherein the means for measuring comprises:

means for suspending delivery of therapeutic stimulation during each of the measurement sessions;

means for controlling measurement of the electrical parameter for a different one or more of the combinations during each of the measurement sessions; and means for resuming the delivery of the therapeutic stimulation to the patient via at least some of the electrodes between consecutive measurement sessions.

24. The system of claim 23, wherein the means for measuring an electrical parameter comprises means for measuring an impedance.

25. The system of claim 23, further comprising means for providing lead functionality information to a user based on the lead functionality test.

26. The system of claim 23, wherein a duration of each of the sessions is within a range from approximately 200 microseconds to approximately five minutes.

* * * * *

UNITED STATES PATENT AND TRADEMARK OFFICE
CERTIFICATE OF CORRECTION

| | | |
|---|---|---|
| PATENT NO. | : 7,623,919 B2 | Page 1 of 1 |
| APPLICATION NO. | : 11/414536 | |
| DATED | : November 24, 2009 | |
| INVENTOR(S) | : Goetz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this

Fourteenth Day of December, 2010

David J. Kappos
*Director of the United States Patent and Trademark Office*